United States Patent [19]

Walker et al.

[11] Patent Number: 4,956,513

[45] Date of Patent: Sep. 11, 1990

[54] RECOVERY OF BF$_3$ FROM OLEFIN OLIGOMER PROCESS

[75] Inventors: Howard W. Walker; Ronny W. Lin, both of Baton Rouge, La.

[73] Assignee: Ethyl Corporation, Richmond, Va.

[21] Appl. No.: 258,387

[22] Filed: Oct. 17, 1988

[51] Int. Cl.$^5$ ................................................ C07C 2/08
[52] U.S. Cl. .................................. 585/525; 585/868; 203/12
[58] Field of Search ............... 585/525, 510, 809, 833, 585/868; 203/12

[56] References Cited

U.S. PATENT DOCUMENTS

| | | | |
|---|---|---|---|
| 2,357,926 | 9/1944 | Bannon | 585/525 |
| 3,763,244 | 10/1973 | Shubkin | 585/525 |
| 3,780,128 | 12/1973 | Shubkin | 585/525 |
| 4,420,647 | 12/1983 | Hammond et al. | 585/525 |
| 4,434,309 | 2/1984 | Larkin et al. | 585/525 X |
| 4,527,004 | 7/1985 | Sweeney | 585/833 X |

FOREIGN PATENT DOCUMENTS

| | | | |
|---|---|---|---|
| 584426 | 1/1947 | United Kingdom | 585/525 |
| 804070 | 11/1958 | United Kingdom | 585/525 |

*Primary Examiner*—Patrick P. Garvin
*Assistant Examiner*—George R. Fourson
*Attorney, Agent, or Firm*—David M. Bunnell; Joseph D. Odenweller

[57] ABSTRACT

A process for recovering BF$_3$ from a BF$_3$-promoter catalyzed α-olefin oligomerization process is disclosed wherein the oligomer reaction product is water washed to extract BF$_3$ as its hydrate and any water soluble promoter and the water extract is distilled to remove components boiling below BF$_3$ hydrate overhead leaving a residual product which is at least 50 weight percent BF$_3$ in the form of BF$_3$ hydrate.

22 Claims, No Drawings

RECOVERY OF BF₃ FROM OLEFIN OLIGOMER PROCESS

BACKGROUND

Alpha-olefin oligomers and their use as hydraulic fluids and synthetic lubricants (synlubes) are well known. U.S. Pat. No. 2,937,129 reports the oligomerization of $C_{5-14}$ α-olefins using a dialkyl peroxide catalyst to make a synlube. U.S. Pat. No. 3,113,167 describes an α-olefin oligomer process using a titanium halide and an aluminum compound as the oligomerization catalyst.

The preferred catalysts for making α-olefin oligomers are Friedel Crafts catalysts such as $BF_3$ as disclosed in U.S. Pat. No. 3,149,178. Optimum properties are obtained starting with 1-decene although mixtures of α-olefins have been used, cf. U.S. Pat. No. 3,330,883.

The preferred Friedel Crafts catalyst is $BF_3$. Pure $BF_3$ is not an effective oligomerization catalyst. A small amount of polar compound is necessary as a promoter. U.S. Pat. No. 3,382,291 describes the use of alcohol promoters such as decanol. Other reported promoters are modenite (hydrogen form), water, phosphoric acid, fatty acids (e.g. valeric acid), ketones, organic esters, ethers, polyhydric alcohols, silica gel and the like.

The most common catalyst, $BF_3$, can present a disposal problem. Various methods have been devised for removing $BF_3$ from an oligomerization reaction to achieve an environmentally acceptable result. Vogel et al. U.S. Pat. No. 4,454,366 and U.S. Pat. No. 4,384,162 describe the use of polyvinyl alcohol to remove $BF_3$ from an oligomerization reaction. Vogel et al. U.S. Pat. No. 4,433,197 contacts the reaction product with silica to remove the $BF_3$. Morganson et al. U.S. Pat. No. 4,429,177 and Madgavkar et al. U.S. Pat. No. 4,213,001 and U.S. Pat. No. 4,308,414 use silica as an absorbant for $BF_3$ in an oligomerization process. Madgavkar et al. U.S. Pat. No. 4,394,296 describe the use of wet silica as a co-catalyst with $BF_3$ in an oligomer process. The silica can be filtered off and recycled as the catalyst. Madgavkar et al. U.S. Pat. No. 4,263,467 remove $BF_3$ by trickling the reaction product over an inert metallic or ceramic bed whereby the $BF_3$ is said to evaporate and can be recovered.

From this it can be seen that a great deal of effort has gone into developing a method for removing $BF_3$ from an olefin oligomerization process in an environmentally safe manner.

SUMMARY

It has now been discovered that $BF_3$ can be recovered from a $BF_3$ catalyzed olefin oligomerization reaction mixture by extracting the $BF_3$ with water and distilling the water from the extract together with any co-catalysts that might be present until an aqueous concentrate of $BF_3$ hydrate remains as the liquid residual product. Boron trifluoride can be recovered from the aqueous concentrate by conventional methods such as by treatment with concentrate $H_2SO_4$ or preferably oleum or $SO_3$ which removes the water liberating $BF_3$.

DESCRIPTION OF THE PREFERRED EMBODIMENTS

A preferred embodiment of the invention is a process for recovering $BF_3$ from an α-olefin oligomerization procedure conducted by oligomerizing an α-olefin in the presence of $BF_3$ and a promoter for $BF_3$ which promoter is selected from water, water insoluble promoters or water soluble promoters wherein said water soluble promoters have a boiling point below the boiling point of $BF_3.2H_2O$ or which forms an azeotrope with water having a boiling point below the boiling point of $BF_3.2H_2O$, said process comprising:

(A) water washing the oligomerization mixture after completing the oligomerization procedure to extract $BF_3$ as a $BF_3$ hydrate together with any water soluble promoter used in the procedure and (B) distilling water and water soluble promoter, if any, from the resultant wash water leaving as the residue a concentrated aqueous $BF_3$ hydrate solution.

Methods of conducting a $BF_3$ catalyzed oligomerization process are well-known. In one mode, $BF_3$ is merely bubbled through the α-olefin reaction mixture during the oligomerization. In a preferred mode, the process is conducted under $BF_3$ pressure. A useful pressure is about 1–100 psig, preferably 5–50 psig and more preferably about 10–20 psig.

Any of the known promoters for $BF_3$ can be used such as water, alcohol (e.g. methanol, ethanol, n-propanol, isopropanol, n-butanol, isobutanol, n-hexanol, 2-ethyl hexanol, n-decanol, n-dodecanol and the like including mixtures thereof), fatty acids (e.g. valeric, caproic and the like), organic esters (e.g. butyl acetate, methyl valerate, ethyl octanoate, and the like), ketones (e.g. methyl ethyl ketone, methyl isobutyl ketone, and the like), ethers (e.g. dibutyl ether, tetrahydrofuran, dioxane and the like), alkoxylated alcohols (e.g. 2-ethoxyethanol, and the like), polyhydric alcohols (e.g. glycol, glycerol and the like), inorganic acids (e.g. phosphoric and the like), silica, zeolites and the like.

In the present process the promoter should either be water, a water insoluble promoter or a water soluble promoter wherein the water soluble promoter has a boiling point below $BF_3.2H_2O$ or which forms an azeotrope with water having a boiling point below that of $BF_3.2H_2O$. These include alcohols, organic esters, ethers, organic acids, ketones and aldehydes. Examples are ethanol, n-butanol, isooctanol, diethyl ether, diisobutyl ether, anisole, n-butyl formate, ethyl acetate n-butyl acetate, amyl acetate, ethyl isobutyrate, propionic acid, methyl ethyl ketone, methyl isobutyl ketone, furfural and the like.

The preferred promoters having these properties are water and alcohols containing about 1–8 carbon atoms such as methanol, ethanol, isopropanol, n-propanol, n-butanol, isobutanol, n-hexanol and n-octanol. The more preferred promoters are alcohols containing about 2–5 carbon atoms. The most preferred promoter is n-butanol.

The amount of promoter should be an amount that causes the $BF_3$ to act as an oligomerization catalyst. This is referred to as a promoter amount. A useful range is about 0.1–2.0 weight percent of the α-olefin.

Alpha-olefins useful in the process are those containing about 8–12 carbon atoms such as 1-octene, 1-decene, 1-dodecene and the like including mixtures thereof. The most preferred α-olefin is 1-decene or an olefin mixture containing mainly, for example, at least 75 weight percent 1-decene.

The preferred reaction temperature is about 20°–50° C. and more preferably about 25°–40° C. Superior results have been achieved at about 30° C. Lower temperatures will increase the amount of higher oligomers but at the cost of a slower reaction rate. High temperatures give a fast reaction rate but increased yield of dimer.

The amount of $BF_3$ in the reaction mixture should be in excess of the amount required to complex with the promoter. This can be accomplished by saturating the reaction mixture with $BF_3$ such as by continuously bubbling $BF_3$ through the reaction mixture. More preferably the reaction is conducted in a closed vessel under $BF_3$ pressure. A useful pressure range is about 1–100 psig, preferably 5–50 psig and most preferably 10–20 psig.

Following the oligomerization the $BF_3$ is extracted with water. Preferably the water washing is conducted using several increments of water such that the first 1 or 2 extractions contain most of the $BF_3$. Later water washings can be disposed of by alternate methods.

The amount of water is about 1–100 parts by weight per 100 parts of oligomer. Preferably the first water wash uses only about 4–10 parts per 100 parts of oligomer. Later washes can use much more water.

Most preferable, both the first and second water wash use only 4–10 parts of water each per 100 parts oligomer. This generally removes at least 90% of the $BF_3$. Subsequent water washes can use much more water, for example 10–20 parts per 100 parts of oligomer to remove the last traces of $BF_3$.

The water extracts containing the major part of the $BF_3$ are then distilled to remove water together with any promoter. For example, n-butanol forms an azeotrope that is 38 weight percent water and 62 weight percent n-butanol and boils at 92.4° C. (atmospheric pressure).

The distillation is conducted to remove water and promoter as a distillate leaving a residual product containing about 50–65 weight percent $BF_3$ as $BF_3.2H_2O$. The distillation is conducted at a temperature below that at which substantial hydrolysis of the $BF_3$ occurs. The distillation can be conducted at atmospheric or at reduced pressure. When conducted at reduced pressure, the preferred reduced pressure is about 10–300 torr, more preferably 10–200 torr and most preferably 50–100 torr.

Promoters that are soluble in water such as ethanol and those having limited solubility in water (e.g. n-butanol, isopentanol) will be extracted into the wash water. The soluble promoters should boil below $BF_3.2H_2O$ or form azeotropes that boil below $BF_3.2H_2O$.

When the distillation liquid residual product reaches the desired concentration of $BF_3$, preferably at least 50 weight percent $BF_3$, the distillation is discontinued. $BF_3$ can be recovered from the residual product by conventional means such as by carefully mixing the residual product with oleum or sulfur trioxide.

In a preferred mode of operation, aqueous wash from a $BF_3$-alcohol catalyzed olefin oligomerization containing about 5–10 weight percent $BF_3$ is continuously conducted to a mid-point in a distillation column operated at 10–300 torr, more preferably 50–100 torr, with the overhead temperature maintained at a temperature below the boiling point of $BF_3.2H_2O$ at that pressure and the reboiler maintained near the boiling point of $BF_3.2H_2O$ at the reboiler pressure. Aqueous distillate removed overhead goes to disposal and residual liquid from the reboiler goes to $BF_3$ recovery.

The following example shows how the process can be conducted.

EXAMPLE 1

A decene oligomer was made by charging 250 parts by weight of 1-decene to a reaction vessel and pressurizing the vessel to 20 psig with $BF_3$ and stirring at 30° C. During the first hour 1.5 parts (0.6 wt %) of n-butanol was added. Stirring was continued at 30° C. for 0.5 hours and then 15 parts of n-butanol were added. Stirring was continued under $BF_3$ pressure for an additional hour (2.5 hours total reaction time).

The $BF_3$ was vented and the reaction mixture was washed with 145 parts of water. The water wash separated and was removed. A second water wash (45 parts) was added to the reaction mixture and, after agitation, it was separated. These two water washes were combined and analyzed for boron, fluoride and n-butanol.

| boron | 1.13 wt % |
|---|---|
| fluorine | 5.7 wt % |
| n-butanol | 5.83 wt % |

Then 9.377 Kg of the combined wash was placed in a 12 L glass distillation vessel and distilled under vacuum starting at 80 torr, 41°–45° C. overhead, to remove an aqueous distillate phase. The aqueous distillate initially split to form a Water phase and an upper n-butanol phase. After about 4 hours, 1886 g of distillate (548 g n-butanol phase, 1328.3 water phase, pH=6–7) had been removed. Distillation was continued the next day starting at 60 torr, 39° C. overhead, and continued for 8.5 hours. Distillation was resumed the next day at 50 torr, 36° C., and continued for 6.5 hours. Distillation was stopped (50 torr, overhead 36° C., reboiler 107° C.) leaving 942 g of a fuming liquid residual product. Analysis of the residual liquid gave: 9.8 weight percent B, 50.7 weight percent F. Normalizing these values gives 16.1 weight percent B, 83.9 percent F. Theory for $BF_3$ is 15.9 weight percent B which is quite close to the 16.1 weight percent by analysis indicating the residual product is about 61 weight percent $BF_3$. Theory for $BF_3.2H_2O$ is 65.3 weight percent $BF_3$. Gaseous $BF_3$ can readily be recovered by carefully mixing the residual liquid with oleum or sulfur trioxide.

EXAMPLE 2

This experiment shows the recovery of $BF_3.2H_2O$ from wash water in a continuous distillation column.

The distillation apparatus comprised a monel distillation pot (reboiler) and a 1" diameter × 15" high polyvinylidene fluoride (Kynar) column packed with cut ¼" Teflon tubing. The wash water feed tap was located at the column mid-point. The initial charge to the reboiler was made up by dissolving 347 g $BF_3$ in 817 g of the combined wash water prepared in Example 1. This gave a 35 weight percent $BF_3$ solution. Then 493 g of this 35 weight percent $BF_3$ solution was placed in the monel reboiler.

The reboiler liquid was heated to 58° C. and the overhead pressure was reduced to 80 torr. Liquid began to distill. After about 20 minutes wash water feed (prepared in Example 1) was started at slightly above the rate of distillate removal and concentrated $BF_3$ aqueous solution was accumulated in the reboiler. Distillation was continued for a total of 64 hours excluding overnight shut-downs. Reboiler temperature rose from 60° C. to 96° C. Overhead pressure was held at 80 torr and overhead distillate was removed at 42° C. The following summarizes the process.

| Initial charge | 493 g 35.4% BF$_3$ |
|---|---|
| Total wash water feed | 8175 g |
| Total distillate | 7355 g |
| Total liquid bottoms | 1275 g |
| Total solids | 2.9 g |
| Material balance | 99.6% |

| | wt % B | wt % F |
|---|---|---|
| Liquid Bottoms | 9.38 | 44.0 |
| Theoretical for BF$_3$ | 15.9 | 84.1 |
| Theoretical for BF$_3$.2H$_2$O | 10.4 | 54.9 |

The boron analysis (9.38 wt %) indicates a higher BF$_3$ and BF$_3$.2H$_2$O content than the fluorine analysis (44 wt %). This may be due to some hydrolysis of BF$_3$ but more likely is due to less accuracy in the fluorine analysis. Even with this, the analysis indicates at least 80.1 wt % BF$_3$.2H$_2$O in the liquid bottoms.

EXAMPLE 3

This example shows the continuous distillation of wash water at atmospheric pressure.

The equipment was the same as in Example 2. The initial charge to the monel reboiler was 454.1 g of wash water from Example 1 and 192.9 g BF$_3$. Heat was applied to the reboiler and at 110° C. reboiler, 87° C. overhead, distillation started (2:1 reflux ratio). After 2 hours 14 minutes (reboiler 161° C., overhead 98° C.), wash water feed from Example 1 was started at the column mid-point. Wash water feed was adjusted to be slightly more than distillate removal. The operation was continued for 24 hours excluding overnight shut-downs. The reboiler and overhead temperatures remained constant at 159°-161° C. and 98°-99° C. respectively.

| Initial reboiler charge | 647 g |
|---|---|
| Total wash water feed | 2334 g |
| Total distillate | 2276 g |
| Total liquid bottoms | 567 g |
| Total solids | 108.5 g |
| Material Balance | 99% |

| | wt % B | wt % F |
|---|---|---|
| Liquid Bottoms | 10.0 | 45.2 |
| Theoretical for BF$_3$ | 15.9 | 84.1 |
| Theoretical for BF$_3$.2H$_2$O | 10.4 | 54.9 |

Increased solids were due to corrosion of the monel reboiler at the higher temperature.

As in Example 1, the boron analysis (10.0 wt %) indicates a high BF$_3$ content than the fluoride analyses (45.2 wt %)—62.9 wt % BF$_3$ vs 53.7 wt % BF$_3$. Even using the lower fluoride analysis, the process successfully recovered a liquid residual product that was 82.3 wt % BF$_3$.2H$_2$O.

We claim:

1. A process for recovering BF$_3$ from an α-olefin oligomerization procedure, said procedure being conducted by oligomerizing an α-olefin in the presence of BF$_3$ and at least one promoter for BF$_3$ which promoter is water, a water insoluble promoter, or a water soluble promoter wherein said water soluble promoter has a boiling point below the boiling point of BF$_3$.2H$_2$O, or which forms an azeotrope with water having a boiling point below the boiling point of BF$_3$.2H$_2$O, said process comprising:

(A) water washing the oligomerization mixture after completing the oligomerization procedure to extract BF$_3$ as a BF$_3$ hydrate together with any water soluble promoter used in the procedure and (B) distilling water and water soluble promoter, if any, from the resultant wash water at a temperature below that at which substantial hydrolysis of the BF$_3$ occurs, leaving as a residue a concentrated aqueous BF$_3$ hydrate solution.

2. A process of claim 1 wherein step (B) is conducted at a reduced pressure of 10-300 torr.

3. A process of claim 2 wherein said promoter is an alcohol.

4. A process of claim 3 wherein said alcohol contains 1-8 carbon atoms.

5. A process of claim 4 wherein said alcohol is n-butanol.

6. A process of claim 5 wherein said concentrated aqueous BF$_3$ hydrate contains at least 50 weight percent BF$_3$.

7. A process of claim 5 wherein step (B) is conducted at a reduced pressure of about 50-100 torr.

8. A process of claim 2 wherein said promoter is water.

9. A process of claim 8 wherein said concentrated aqueous BF$_3$ hydrate solution contains at least 50 weight percent BF$_3$.

10. A process of claim 2 wherein the wash water containing BF$_3$ from step (A) is conducted to an intermediate location in a distillation column, said column being maintained under temperature and pressure conditions such that water and components which boil at a lower temperature than BF$_3$ hydrate distill overhead and a concentrated aqueous BF$_3$ hydrate solution descends to the bottom of said distillation column as said residue.

11. A process of claim 10 wherein said promoter is an alcohol.

12. A process of claim 11 wherein said alcohol is n-butanol.

13. A process of claim 12 wherein said residue contains at least 50 weight percent BF$_3$.

14. A process of claim 10 wherein said promoter is water.

15. A process of claim 14 wherein said residue contains at least 50 weight percent BF$_3$.

16. A process of claim 10 wherein said distillation column is maintained at an overhead reduced pressure of about 10-300 torr.

17. A process of claim 16 wherein said promoter is n-butanol.

18. A process of claim 1 wherein step (B) is conducted at a reduced pressure of about 30-100 torr.

19. A process of claim 1 wherein said distillation is conducted at atmospheric pressure.

20. A process of claim 19 wherein said promoter is an alcohol.

21. A process of claim 20 wherein said α-olefin is mainly 1-decene and said alcohol is n-butanol.

22. A process of claim 1 wherein said distillation is conducted at reduced pressure.

* * * * *